United States Patent [19]

Fawcett

[11] Patent Number: 5,988,236
[45] Date of Patent: Nov. 23, 1999

[54] MULTIPLE SYRINGE PUMP ASSEMBLY FOR LIQUID HANDLER

[75] Inventor: Kevin R. Fawcett, Ridgeway, Wis.

[73] Assignee: Gilson, Inc., Middleton, Wis.

[21] Appl. No.: 09/127,307

[22] Filed: Jul. 31, 1998

[51] Int. Cl.[6] ................................................. B67C 3/00
[52] U.S. Cl. .................. 141/130; 141/242; 141/238; 222/173; 222/142; 222/386; 222/276; 222/387; 222/390; 422/65; 422/100; 73/864.17
[58] Field of Search .................................... 222/135, 137, 222/333, 386, 142, 255, 275, 276, 387, 390; 141/130, 234, 236–238, 242–245; 422/63, 65, 99, 100, 103; 73/864.16, 864.17

[56] References Cited

U.S. PATENT DOCUMENTS

| | | | |
|---|---|---|---|
| 3,536,449 | 10/1970 | Astle | 141/130 |
| 4,000,976 | 1/1977 | Kramer et al. | 141/130 |
| 4,042,338 | 8/1977 | Huber | 141/130 |
| 4,199,013 | 4/1980 | Reich et al. | 141/130 |
| 4,422,151 | 12/1983 | Gilson . | |
| 4,478,094 | 10/1984 | Salomaa et al. | 422/65 |
| 4,505,522 | 3/1985 | Tanaka . | |
| 4,598,049 | 7/1986 | Zelinka et al. | 222/137 |
| 5,012,845 | 5/1991 | Averette | 141/130 |
| 5,217,146 | 6/1993 | Neff et al. | 222/137 |
| 5,309,959 | 5/1994 | Shaw et al. | 141/130 |

*Primary Examiner*—J. Casimer Jacyna
*Attorney, Agent, or Firm*—Mason, Kolehmainen Rathburn & Wyss

[57] ABSTRACT

A multiple probe liquid handler includes a syringe pump assembly with multiple syringe pumps communicating with the probes. A carriage movable with respect to a fixed support base carries syringe pump pistons moving within syringe pump cylinders secured to the base. A drive system including a single drive motor has a single drive point connection to the carriage for moving the carriage and operating the syringe pumps in order to draw fluid into or discharge fluid from the multiple probes. A linear motion support assembly includes spaced rails attached to the support base and slides attached to the carriage and riding along the rails. The assembly includes two parallel rails and three slides, one riding along one rail and two riding along the other rail, providing an inexpensive yet imbalance tolerant three point support.

11 Claims, 5 Drawing Sheets

MULTIPLE SYRINGE PUMP ASSEMBLY FOR LIQUID HANDLER

FIELD OF THE INVENTION

The present invention relates to automated liquid handlers and more particularly to a multiple syringe pump assembly for liquid handlers having multiple probes.

DESCRIPTION OF THE PRIOR ART

Automated liquid handlers are used for handling laboratory samples in a variety of laboratory procedures. Liquid handlers are used in automated injector procedures, for example sample preparation for high pressure liquid chromatography, and are also used for biotechnological and pharmaceutical liquid assay procedures and others. A typical automated liquid handler has a tray that supports a number of sample containers such as tubes in one or more racks or an array of numerous sample containing wells in one or more microplates. The typical liquid handler has a probe that can be moved into alignment with a selected container to add or remove liquid to or from the container. A syringe pump can be placed in communication with a reservoir or with the probe. When the syringe pump communicates with the probe, it can be operated in one direction to decrease pressure at the probe to draw liquid, such a sample, a dilutant or a rinse, or to draw aspirating air into the probe. The syringe pump can be operated in the other direction increase pressure at the probe to expel liquid or air from the probe.

In many laboratory procedures it is an important goal to perform many operations as quickly as possible. One approach to increasing throughput in microplate replication, screening assays and the like is to provide multiple probes. However each of the multiple probes requires a dedicated syringe pump. The requirement for a syringe pump assembly having multiple syringe pumps has led to problems in the past. Using an independent drive motor and drive point for each syringe would be very expensive. Driving a number of syringe pumps with a single drive motor is less expensive, but guiding a number of syringe pumps in simultaneous movement with accurate control and without binding has been difficult. In addition, unbalanced conditions can arise if one or fewer than all possible syringe pumps or syringe pumps of different capacities are used. Such unbalanced conditions cause serious problems in providing smooth, reliable linear motion of known multiple syringe pump assemblies.

SUMMARY OF THE INVENTION

A principal object of the present invention is to provide an improved syringe pump assembly for multiple probe liquid handlers. Other objects of the invention are to provide a syringe pump assembly in which a single drive motor acting at a single drive point accurately and smoothly drives a number of syringe pumps; to provide an assembly in which an unbalanced condition using one or fewer than all the syringe pumps does not adversely effect pump movement; to provide a syringe pump assembly in which syringes of different sizes may be used simultaneously; and to provide a syringe pump assembly for a multiple probe liquid handler that overcomes problems of known multiple syringe pump assemblies.

In brief, in accordance with the invention there is provided a syringe pump assembly for an automated liquid handler having a sample tray supporting an array of numerous sample containers and a plurality of probes movable into alignment with a like plurality of the sample containers. The syringe pump assembly includes a fixed support and a plurality of syringe pumps each adapted to be in pressure communication with one of the plurality of probes. Each syringe pump includes a pair of pumping members including a cylinder and piston slidable within the cylinder, the cylinders being parallel to one another. The assembly includes a carriage. One member of each pumping pair is secured to the fixed support and the other member of each pumping pair is secured to the carriage. Power means including a single drive motor is supported by the fixed support and connected to the carriage for providing a motive force for moving the carriage. A mounting system supports the carriage on the fixed support for linear movement in a direction parallel to the cylinders. The mounting system includes a pair of spaced apart guide rails mounted parallel to one another and to the cylinders and a plurality of slides riding along the rails. The rails are attached to either the fixed support or the carriage, and the slides are attached to the other.

BRIEF DESCRIPTION OF THE DRAWING

The present invention together with the above and other objects and advantages may best be understood from the following detailed description of the preferred embodiment of the invention illustrated in the drawings, wherein.

DETAILED DESCRIPTION OF THE PREFERRED EMBODIMENTS

Figure 1:
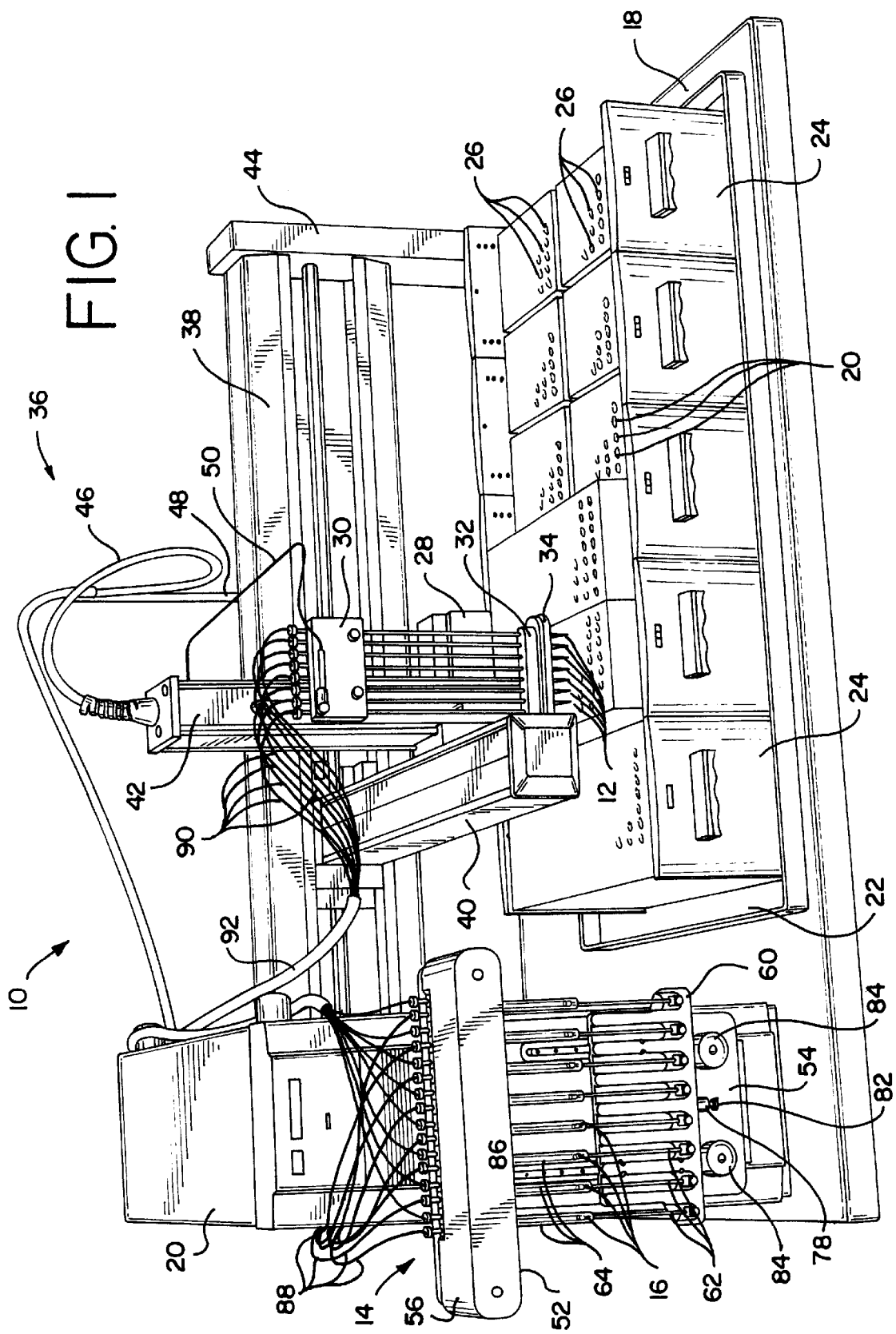
FIG. 1 is a perspective view of an automated multiple probe liquid handler having a syringe pump assembly constructed in accordance with the present invention.

Having reference now to the drawings, in FIGS. 1 there is illustrated an automated liquid handler designated as a whole by the reference numeral 10. The liquid handler 10 has multiple probes 12, preferably eight in number, although a different number of probes could be used. The liquid handler includes a syringe pump assembly generally designated as 14 constructed in accordance with the principles of the present invention. The assembly 14 includes a syringe pump 16 corresponding to each of the multiple probes 12.

The automated liquid handler 10 seen in FIG. 1 includes a base 18 with a housing 20 at one end. The base 18 supports a tray 22 upon which are supported one or more racks 24 holding numerous containers 26 for containing liquid samples and/or other liquids. The tray 22 accommodates various types and combinations of racks such as racks for supporting vials and vessels and modular reservoirs of different sizes and types, and racks for containing microplates having an array of numerous sample containing wells, such as for example arrays of ninety-six or three hundred eighty-four wells. In the illustrated embodiment of the invention, the tray 22 supports racks 24 containing an array of numerous containers 26 of a variety of capacities. Tray 22 also supports a probe rinse station 28, and in some configurations the tray 22 may support injection ports for high pressure liquid chromatography (HPLC) assemblies.

Each probe 12 is a hollow tube, and the probes 12 are ganged together and held for simultaneous movement in a planar array by a probe holder 30. The lower ends of the probes 12 are guided by a probe guide 32 carried by a Z drive foot 34. The spacing between probes 12 corresponds to the spacing between containers 26. The array of probes 12 is moved relative to the containers 26 supported in racks 24 on tray 22 by a transport system 36 including an X arm 38, a Y arm 40 and a Z arm 42. The transport system 36 locates the probes 12 precisely in a three coordinate system including X, Y and Z coordinates. The probes 12 can be located above any corresponding liquid containers 26 or above the rinse station 28 or HPLC injection ports, and the probes 12 can be raised and lowered relative to the containers 26, rinse station 28 or injection ports.

The X arm 38 is supported in a fixed position extending behind and above the tray 22 between the housing 20 and an end support 44. The Y arm 40 extends forward from the X arm 38 over the tray 22. An X drive motor associated with the X arm 38 moves the Y arm 40 in the X direction along the length of the tray 22. The Z arm 42 is supported by the Y arm 40 and extends vertically in the Z direction. A Y drive motor associated with the Y arm 40 moves the Z arm 42 in the Y direction across the width of the tray 22. The probes 12 in the probe holder 30 are carried by the Z arm 42 and are moved in the vertical Z direction by a Z motor associated with the Z ARM 42. A Z drive control cable 46 supported by a rod 48 extends from the housing 20 to the Z arm 42. A liquid level sensing cable 50 extends between the Z arm 42 and the probe holder 30. A further description of the transport system 36 and other elements of the liquid handler 10 beyond that helpful to an understanding of the present invention can be found in U.S. Pat. No. 4,422,151, incorporated herein by reference.

The syringe pump assembly 14 of the present invention is illustrated in more detail in FIGS. 2–7. The assembly includes a generally L-shaped fixed support 52 with a flat, planar vertical base portion 54 and a horizontally projecting upper valve retainer portion 56. A motor drive assembly 58 (FIGS. 2 and 4) is located within and at the front of the housing 20, and the base portion 54 is secured to the front of the housing 40 and overlies the motor drive assembly.

A slide or carriage 60 is mounted for sliding movement upon the base portion 54 of the fixed support 52. Each syringe pump 16 includes a pair of cooperating pumping members, a syringe piston 62 movable within a syringe cylinder 64. The carriage 60 includes a number of piston mounting stations or nests 66, one for receiving each of the pistons 62. Each station 66 includes a female threaded opening where a piston may be secured by a threaded fastener 68. The valve retainer portion 56 of the fixed support 52 includes a number of cylinder retainer stations 70 in the form of female threaded ports into which the ends of the cylinders 64 may be connected. The stations 70 are preferably valve ports of flow control valves mounted within the valve retainer. In the illustrated embodiment of the invention there are eight piston and cylinder mounting stations 66 and 70 for mounting eight syringe pumps 16 corresponding to the eight probes 12. The principles of the invention are applicable to systems with more or fewer probes and syringe pumps.

Figure 2:
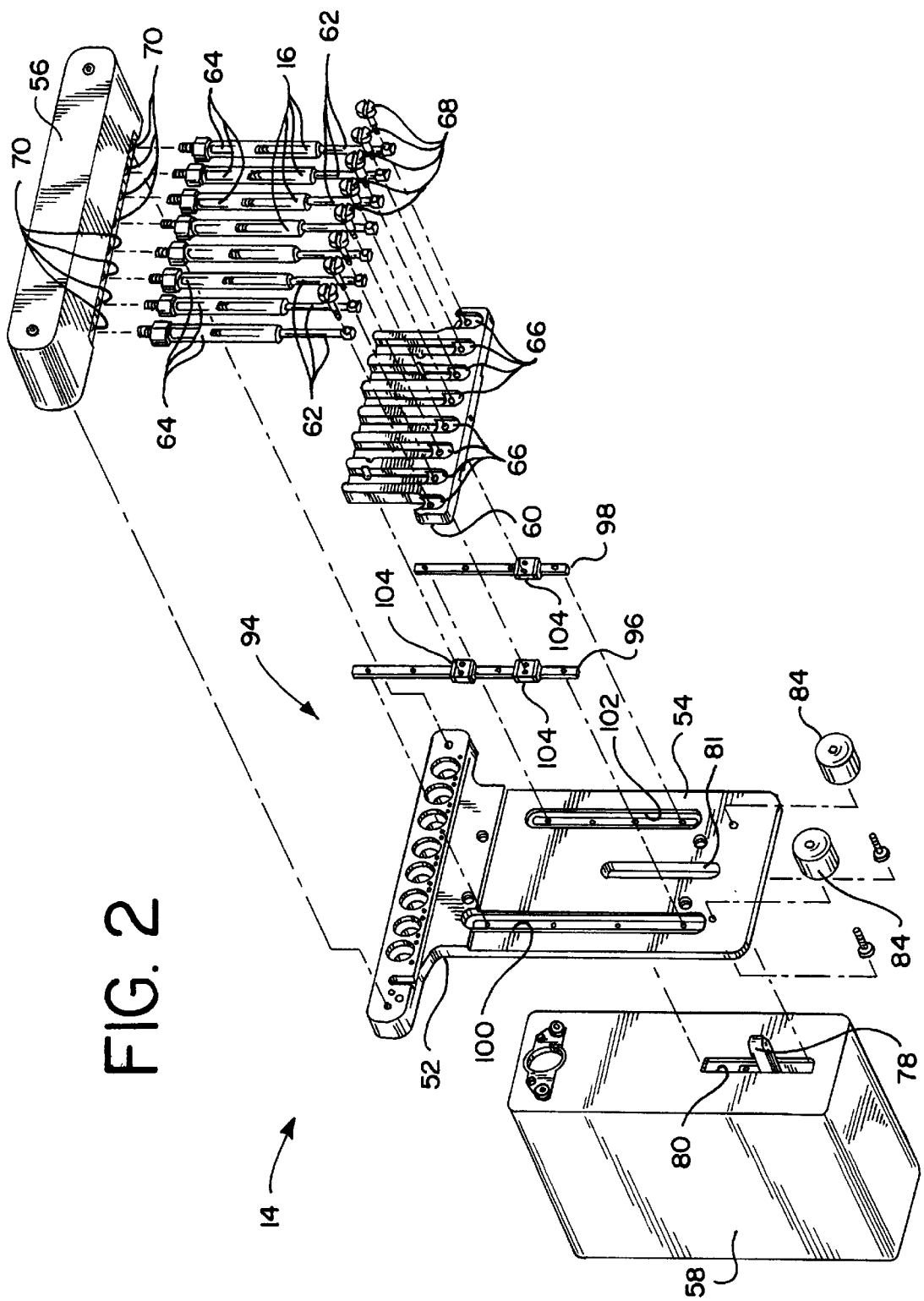
FIG. 2 is an exploded isometric view of the syringe pump assembly.
Figure 3:
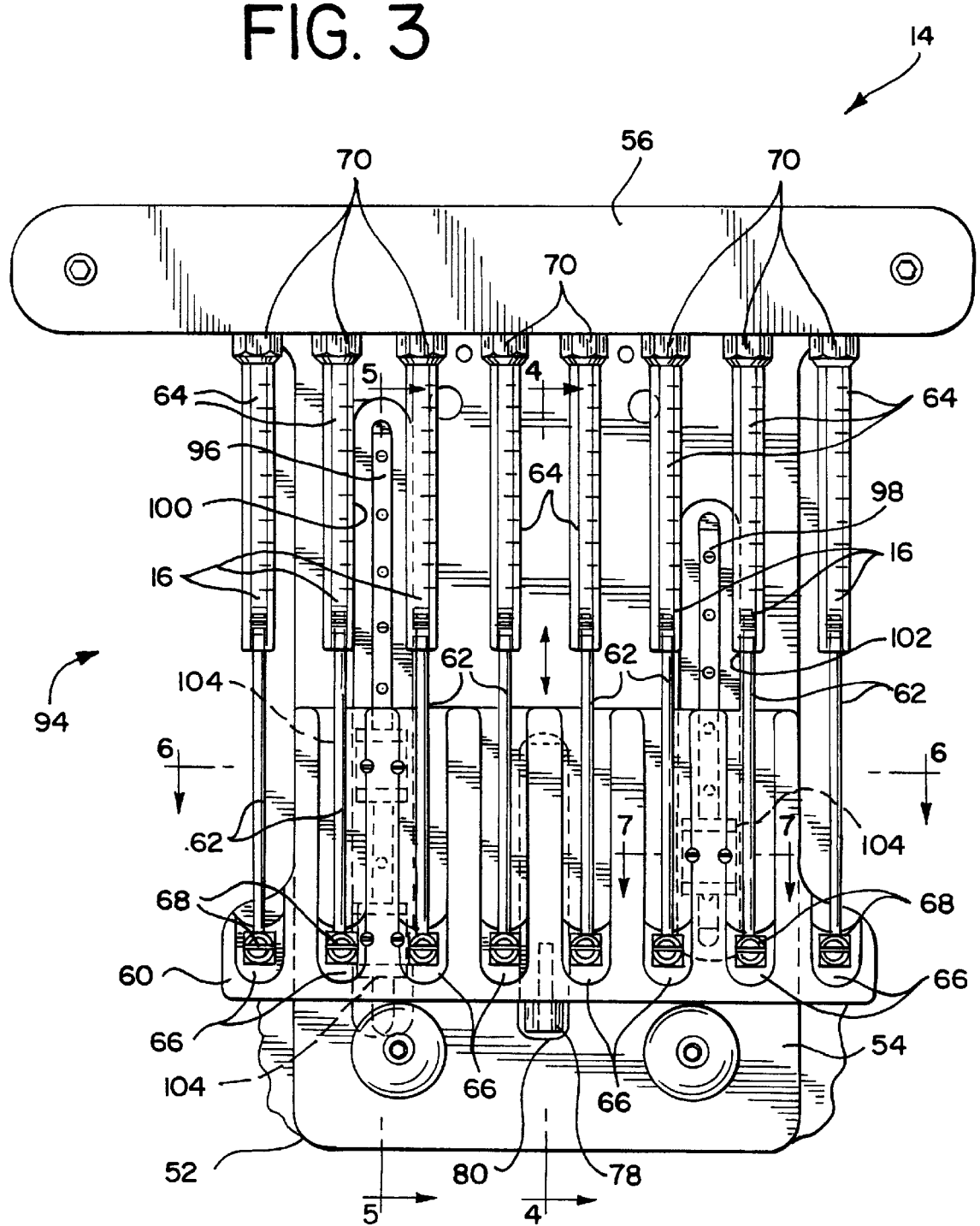
FIG. 3 is front elevational view of the syringe pump assembly.
Figure 4:
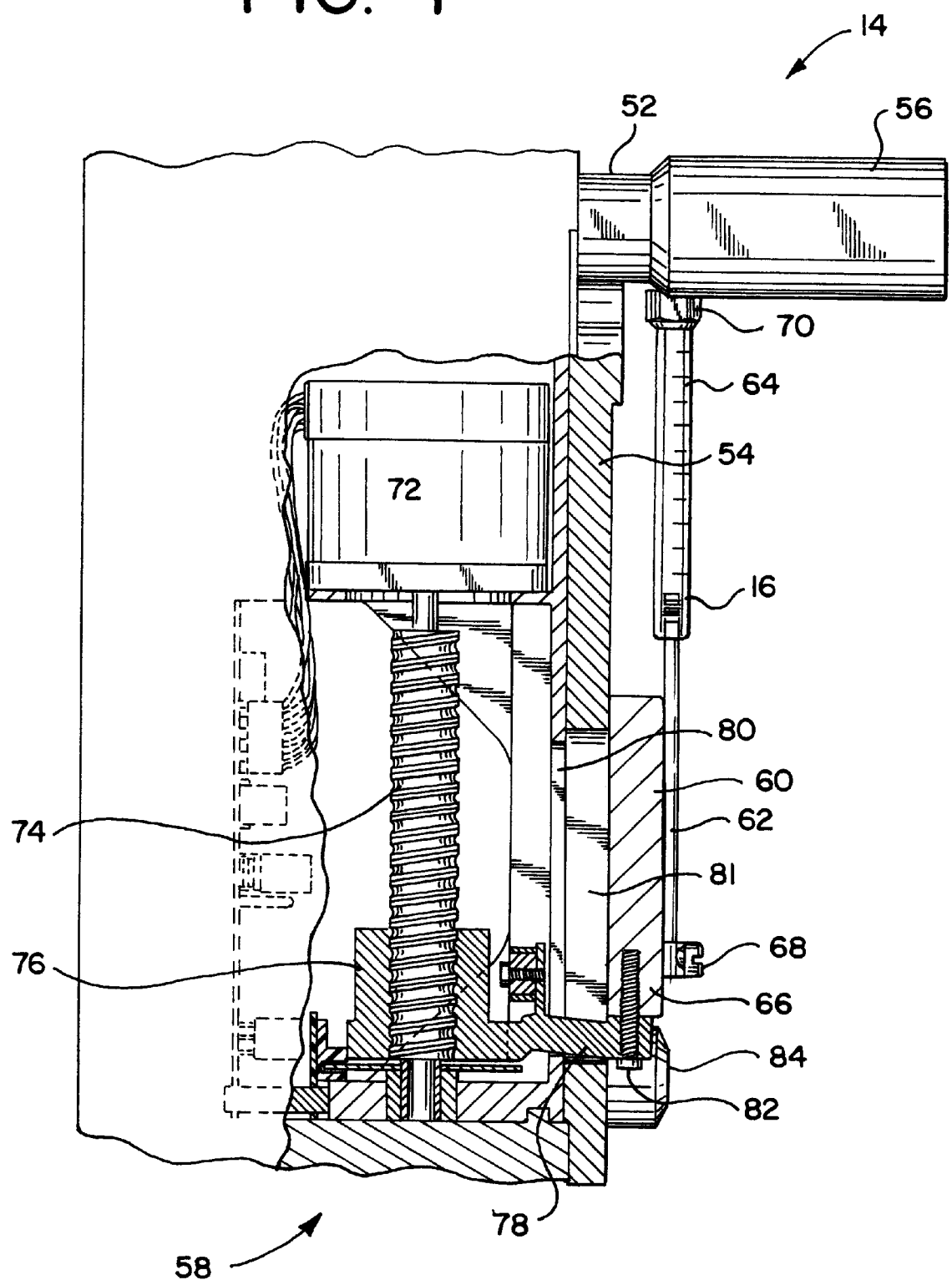
FIG. 4 is a sectional view taken along the line 4—4 of FIG. 3.

Motor drive assembly 58 (FIGS. 2 and 4) includes a single drive motor 72 supplying motive power for moving the carriage 60. The motor 72 is reversible and rotates a drive screw 74 in alternate directions. A screw follower 76 is moved axially in opposite directions in response to rotation of the drive screw 74. The follower has a drive projection 78 extending forward through a slot 80 in the front wall of the housing 20 and a slot 81 in the base portion 54 (FIG. 2). The projection 78 is attached by a fastener 82 to the carriage 60 to provide a single point drive for moving he carriage relative to the base portion 54 of the fixed support 52 in response to operation of the drive motor 72.

As the carriage 60 moves upward, pistons 62 move upward within the fixed cylinders 64 decreasing the volume within the cylinders 64. As the carriage 60 moves downward, the resulting piston movement increases the volume within the cylinders. Downward movement of the carriage 60 is limited by engagement of the carriage 60 with a pair of stops 84 secured to the base portion 54. The interiors of the cylinders communicate with the ports at the cylinder retaining stations 70. The valve retainer portion 56 includes two upwardly directed ports 86 selectively communicating with each retaining station port 70. A valve associated with each syringe pump 16 places the cylinder 64 and port 70 into communication with a selected one of the ports 86. As seen in FIG. 1, one of each pair of ports 86 communicates through a reservoir tube 88 with a reservoir or container of water or other dilutant or liquid. The other port 86 of each pair communicates through a needle tube 90 with a corresponding one of the multiple probes 12. The needle tubes 90 are arranged in a bundle 92 for part of their travel.

Downward movement of the carriage 60 and pistons 62 results in a reduction in pressure in either the reservoir tubes 88 or in the needle tubes 90 and probes 12. This pressure reduction can be used for example to draw a dilutant into the tubes 88 or to draw liquid samples from containers 26 or a rinse liquid from rinse station 28 into the probes 12. Conversely, upward movement of the carriage 60 and pistons 62 results in an increase in pressure that can be used for example to discharge liquid or air from the probes 12.

Figures 5, 6, 7:
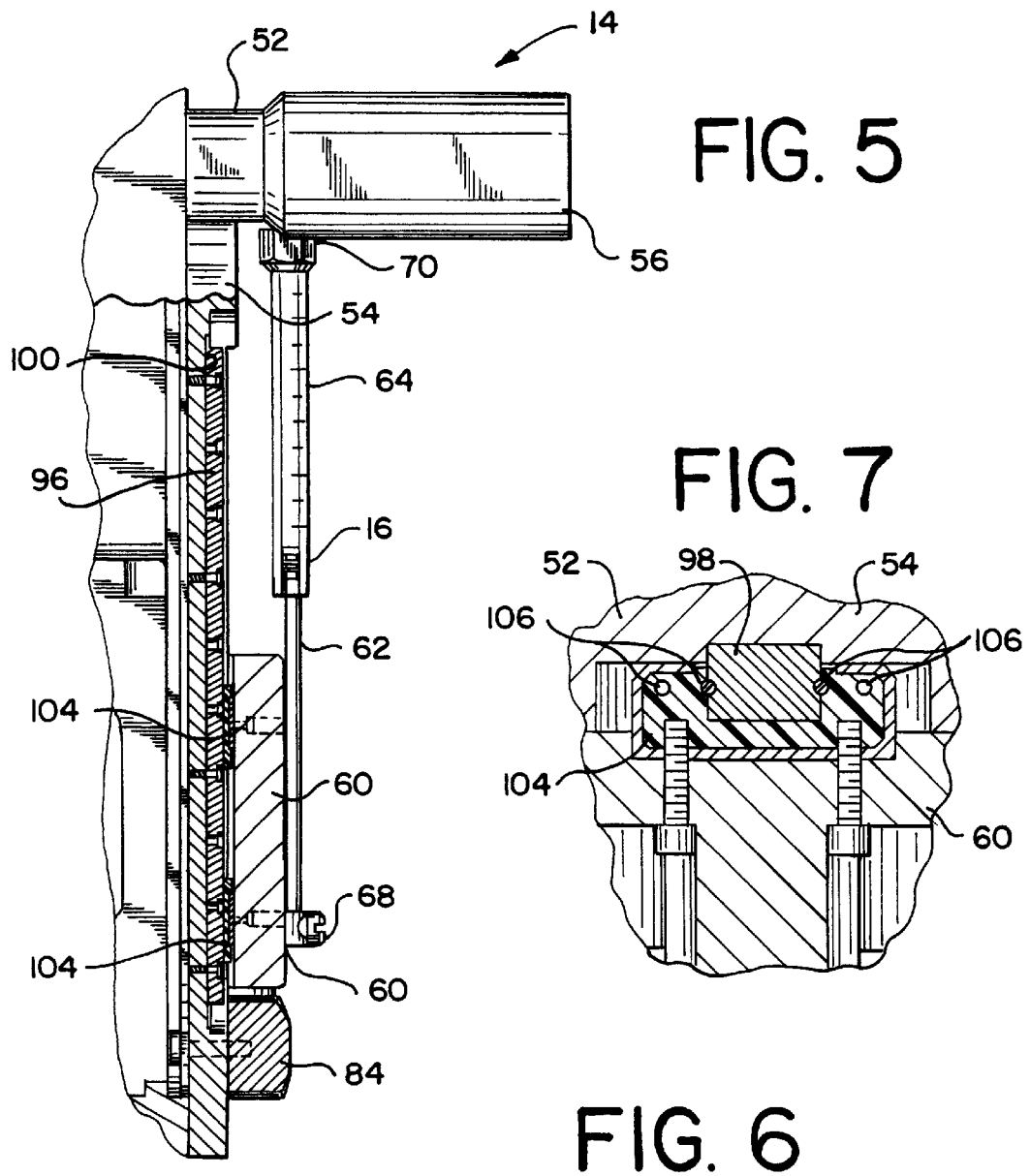
FIG. 5 is a sectional view taken along the line 5—5 of FIG. 3.
FIG. 6 is a sectional view taken along the line 6—6 of FIG. 3.
FIG. 7 is an enlarged sectional view taken along the line 7—7 of FIG. 3.

In accordance with the present invention, a linear motion support assembly 94 supports the carriage 60 for movement relative to the base portion 54. A pair of parallel guide rails 96 and 98 are secured to the base portion 54 within recesses 100 and 102. Slides 104 attached to the carriage 60 ride upon the rails 96 and 98. The rails 96 and 98 are parallel to the axes of the cylinders and pistons 64 and 62 and the carriage 60 reciprocates in this parallel direction. As seen in FIG. 7, the rails have opposed grooves receiving ball bearings 106. A further description of the structural details of the slides 104 and rails 96 and 98 beyond that needed for an understanding of the present invention may be found in U.S. Pat. No. 4,505,522 incorporated herein by reference.

It is preferred that the support assembly 94 include three and not more than three slides 104, with two slides 104 riding along one rail 96 and a single slide riding along the other rail 98. This provides a three point, triangular support of the carriage 60, preventing possible misalignment and binding of the carriage as it moves. In addition, the rail 98 carrying a single slide 104 is shorter than the rail 96.

The linear motion support assembly 94 of the present invention has important advantages. It accommodates a relatively inexpensive single point drive yet is highly tolerant of unbalanced conditions. As a result, it is not necessary to use all eight syringe pumps 16 in order to balance resistance on both sides of the single drive point established by the drive projection 78. Even if a single syringe pump 16 is used in an outboard position, a condition that maximizes imbalance, the carriage moves freely without binding. Accordingly any number of syringe pumps in any desired positions can be successfully used. In addition, it is possible to use syringe pumps 16 of different capacities in different locations at the same time.

While the present invention has been described with reference to the details of the embodiment of the invention shown in the drawing, these details are not intended to limit the scope of the invention as claimed in the appended claims.

What is claimed is:

1. A syringe pump assembly for an automated liquid handler having a sample tray supporting an array of numerous sample containers and a plurality of probes movable into alignment with a like plurality of the sample containers, said syringe pump assembly comprising:

a fixed support;

a plurality of syringe pumps each adapted to be in pressure communication with one of the plurality of probes;

each syringe pump including a pair of pumping members including a cylinder and piston slidable within said cylinder, said cylinders being parallel to one another;

a carriage;

one member of each pumping pair being secured to said fixed support and the other member of each pumping pair being secured to said carriage;

power means including a single drive motor supported by said fixed support and connected to said carriage for providing a motive force at a single drive point for moving said carriage; and a mounting system for supporting said carriage on said fixed support for linear movement in a direction parallel to said cylinders;

said mounting system including a pair of spaced apart guide rails mounted parallel to one another and to said cylinders and a plurality of slides riding along said rails;

said rails being attached to one of said fixed support and said carriage, and said slides being attached to the other of said fixed support and said carriage;

said plurality of slides including one slide riding along one of said rails and two slides riding along the other of said rails.

2. A syringe pump assembly as claimed in claim 1, said plurality of slides consisting of one slide riding along one of said rails and two slides riding along the other of said rails.

3. A syringe pump assembly as claimed in claim 1, said cylinders being secured to said fixed support and said pistons being secured to said carriage.

4. A syringe pump assembly as claimed in claim 1, said rails being attached to said fixed support and said slides being attached to said carriage.

5. A syringe pump assembly for a multiple probe automated liquid handler; said syringe pump assembly comprising:

a support having a generally planar base portion and a valve retainer portion projecting from said base portion;

a carriage supported on said base portion for movement toward and away from said valve retainer portion;

a plurality of syringe pump stations defined by said carriage and said valve retainer portion, each syringe pump station including a piston retainer defined on said carriage and a cylinder retainer defined on said valve retainer in alignment with said corresponding piston retainer;

a plurality of conduit connectors defined on said valve retainer for attachment to conduits for providing flow paths from said piston retainers to the multiple probes; and a support assembly for supporting said carriage on said base portion for linear motion;

said support assembly including a pair of parallel spaced apart rails mounted in recessed positions in said base portion and a plurality of slides attached to said carriage and riding upon said rails;

one of said rails being shorter than the other of said rails, and said slides consisting essentially of one slide riding upon said shorter rail and two slides riding upon said longer rail.

6. The syringe pump assembly of claim 5, said syringe pump stations being arrayed parallel to one another across the width of said carriage, and said rails being separated by a distance equal to a plurality of said syringe pump stations.

7. The syringe pump assembly of claim 6 wherein there are eight syringe pump stations and said rails are separated by at least four said syringe pump stations.

8. The syringe pump assembly of claim 5, each said cylinder retainer comprising a female threaded opening in said valve retainer portion.

9. The syringe pump assembly of claim 8, each said piston retainer comprising a threaded structure for receiving a mating threaded piston attachment fastener.

10. A multiple probe automated liquid handler comprising:

a housing;

a sample tray on said housing for supporting an array of sample containers;

a probe holder;

a plurality of probes supported by said probe holder;

a probe drive system coupled between said housing and said probe holder for moving said probe holder and said probes into registration with a selected region of said tray a syringe pump assembly including a plurality of syringe pumps;

a plurality of conduits for providing pressure communication between said syringe pumps and said probes;

a carriage;

each syringe pump including a cylinder secured to said housing and a piston secured to said carriage and slidable within said cylinder, said cylinders being parallel to one another;

power means supported by said housing and connected to said carriage for moving said carriage; and a mounting system for supporting said carriage on said housing for linear movement in a direction parallel to said cylinders;

said mounting system including a pair of spaced apart guide rails mounted parallel to one another and to said cylinders and a plurality of slides riding along said rails;

said rails being attached to said housing, and said slides being attached to said carriage;

said slides consisting essentially of three slides, one riding along one said guide rail and two riding along the other said guide rail to provide a triangular support system.

11. A liquid handler as claimed in claim 10 wherein there are eight of said probes and syringe pumps.

* * * * *